United States Patent [19]

Chiu et al.

[11] Patent Number: 5,140,037
[45] Date of Patent: Aug. 18, 1992

[54] TREATMENT OF CENTRAL NERVOUS SYSTEM DISORDERS WITH IMIDAZOLE ANGIOTENSIN-II RECEPTOR ANTAGONISTS

[75] Inventors: Andrew T. Chiu, Landenberg, Pa.; Victor J. DeNoble; John J. V. Duncia, both of Newark, Del.; Pancras C. B. Wong, Wilmington, Del.

[73] Assignee: E. I. du Pont de Nemours and Company, Wilmington, Del.

[21] Appl. No.: 497,063

[22] Filed: Mar. 20, 1990

[51] Int. Cl.$^5$ .............. A01N 43/50; A01N 43/64; A01N 43/52; A01N 35/00

[52] U.S. Cl. .................... 514/381; 514/394; 514/677; 514/679; 514/685; 514/688; 514/235.8; 514/399; 514/397

[58] Field of Search ............... 514/381, 399, 394, 429, 514/688, 679, 235.8, 428, 397

[56] References Cited

U.S. PATENT DOCUMENTS

| | | | |
|---|---|---|---|
| 4,301,169 | 11/1981 | Yamanaka et al. | 424/273 |
| 4,402,966 | 7/1983 | Yamanaka et al. | 424/273 R |
| 4,533,669 | 8/1985 | Yamanaka et al. | 514/396 |
| 4,602,031 | 7/1986 | Yamanaka et al. | 514/399 |
| 4,812,462 | 3/1989 | Blankley et al. | 514/303 |

FOREIGN PATENT DOCUMENTS

| | | |
|---|---|---|
| 22279 | 3/1989 | Australia . |
| 288907 | 11/1988 | European Pat. Off. . |
| 307872 | 3/1989 | European Pat. Off. . |
| 245637 | 11/1989 | European Pat. Off. . |
| 2946020 | 3/1989 | Fed. Rep. of Germany . |

OTHER PUBLICATIONS

Mann, Exp. Brain Res., vol. 4, suppl. p. 242, 1982.
Fitzsimons, Rev. Physiol. Biochem, Pharmacol., vol. 87, p. 117, 1980.
Scholken et al., Experientia., vol. 38, p. 469, 1982.
Koller, et al., Neuroscience Lett., vol. 14, pp. 71–75, 1975.
Morgan and Routtengerg, Science, vol. 196, pp. 87–89, 1977.
Arregui, et al., J. Neurochem, vol. 38, pp. 1490–1492, 1982.
Zubenko, et al., Biol. Psych., vol. 21, pp. 1365–1381, 1986.
Usinger, et al., Drug. Dev. Research, vol. 14, pp. 315–324, 1988.
Costall, et al., Pharmacol, Biochem. Behav., vol. 33, pp. 573–579, 1989.
Barnes, et al., Brain Research, vol. 491, pp. 136–143, 1989.
U.S. application Ser. No. 07/373,755, filed Jun. 30, 1989.
U.S. application Ser. No. 07/375,069, filed Jun. 30, 1989.
Chiu, et al., Biochem and Biophys. Res. Comm., vol. 165, pp. 196–203, 1989.
Whitebread, et al., Biochem and Biophys. Res. Comm., vol. 163, pp. 284–291, 1989.
Unger, et al., Circulation, vol. 77 (Suppl I), pp. 40–54, 1988.
Bennet and Snyder, J. Biol. Chem. vol. 254, pp. 7423–7430, 1976.

Primary Examiner—Frederick E. Waddell
Assistant Examiner—T. J. Criares

[57] ABSTRACT

Substituted imidazoles such as 2-butyl-4-chloro-1-[(2'-(1H-tetrazol-5-yl)biphenyl-4-yl)methyl]-5-(hydroxymethyl)imidazole and 2-butyl-4-chloro-1-[(2'-carboxybiphenyl-4-yl)-methyl]-5-(hydroxymethyl)imidazole and pharmaceutically acceptable salts thereof are useful for treating central nervous system disorders, such as cognitive and learning disorders, mediated by angiotensin II.

26 Claims, No Drawings

TREATMENT OF CENTRAL NERVOUS SYSTEM DISORDERS WITH IMIDAZOLE ANGIOTENSIN-II RECEPTOR ANTAGONISTS

BACKGROUND OF THE INVENTION

Angiotensin II (AII), in addition to being a circulating hormone, is now thought to act as a neuropeptide in the central nervous system (CNS) and may play a modulatory function on the release and subsequent action of other neurotransmitters (Unger et al. (1988) *Circulation* 77 (suppl 1):40-54). Specific receptors for AII with high affinity have been identified and localized in different regions of the CNS (Mann (1982) *Exp. Brain Res.* 4 (suppl):242). Stimulation of AII receptors in the CNS elicits a complex but very reproducible and concerted pattern of behavioral, cardiovascular, and endocrine responses (Fitzsimons (1980) *Rev. Physiol. Biochem. Pharmacol.* 87:117). These include CNS-induced elevation of blood pressure, increased drinking and sodium appetite, release of antidiuretic hormone, oxytocin, luteinizing hormone, and prolactin, and other effects (Scholken et al. (1982) *Experientia* 38:469). The CNS effects of AII could lead to hypertension and other cardiovascular diseases through inhibition of the baroreceptor reflex, increase in salt consumption, volume expansion, and increased peripheral resistance. Besides the cardiovascular system, AII may also influence the reproductive system and other brain functions, such as memory (Koller et al. (1975) *Neuroscience Lett.* 14:71-75).

The major functions of AII in the CNS can be classified into three groups which may share, at least in part, overlapping mechanisms of action. The first major function of AII in the CNS is regulation of body fluid volume in response to hypovolemia, involving, for example, regulation of thirst, blood pressure increases, vasopressin release, sodium appetite increase, adrenocorticotropic hormone (ACTH) release, and aldosterone release (Unger et al. (1988) *Circulation* 77 (suppl 1):40-54, and references cited therein). This CNS function of AII is closely related to the role of AII in hypertension.

A second function of AII in the CNS, although poorly defined, is the regulation of gonadotrophic hormone releasing hormones and pituitary hormones during the reproductive cycle and pregnancy (Unger et al., supra).

A third possible CNS function of AII is a synaptic function. AII appears to interact with neurotransmitters such as acetylcholine (ACh), catecholamines, serotonin, and other peptides (Unger et al., supra). The amount of data supporting this CNS function of AII is limited. Published results suggest that increased AII activity in brain maintains an inhibitory control on cholinergic neurons resulting in impaired cognitive performance.

The role of peptides in learning and memory was initially investigated by DeWied in the late 1960's and early 1970's, and led Morgan and Routtenberg (*Science* (1977) 196:87-89) to investigate the role of AII in mediating retention of a passive avoidance (PA) response in rats. These authors demonstrated that rats injected with AII into the dorsal neostriatum, a brain area that has a high concentration of AII as well as precursors and metabolic enzymes for AII biosynthesis, showed a disruption in retention of a PA response. The authors demonstrated specificity of the response in terms of both the location in the brain and the peptide used (thyrotropin releasing hormone or lysine-8-vasopressin had no effect). This study showed that increased AII in the dorsal neostriatum results in a cognitive impairment which is most likely a result of AII modulation of neuronal activity that is necessary for consolidation of newly acquired information.

A different approach for investigating the behavioral effects of AII in the CNS was taken by Koller et al. *Neuroscience Letters* (1975) 14:71-75. These authors injected renin into the lateral ventricle of the brain (IVT) and measured increases in AII in cerebrospinal fluid (CSF); AII increased from 40 to about 5,000 fmol per mL. This increase in AII was accompanied by a disruption of avoidance learning. These results suggested that renin-stimulated biosynthesis of AII could disrupt memory. IVT administration of the angiotensin-converting enzyme (ACE) inhibitors SQ 14225 (captopril), prior to the resin injection, prevented the renin-induced avoidance disruption. We have also shown in our laboratory that renin administered IVT produces a dose-related amnesia in a PA task, and this renin-induced amnesia can be prevented by IVT administration of the ACE inhibitor captopril. These results suggest that increased AII levels in brain leads to a disruption of avoidance performance. Thus, this amnesia can be achieved by direct application into a discrete brain area of AII or renin, a stimulator of endogenous AII biosynthesis.

In the literature on the neuropathology and neurochemistry of Alzheimer's disease (AD) using human CSF and brain tissue, two reports of altered levels of dipeptidyl carboxypeptidase (angiotensin-converting enzyme, ACE) were published. Arrequi et al. *J. Neurochemistry* (1982) 38:1490-1492 found increased ACE activity in the hippocampus, parahippocampal gyrus, frontal cortex, and caudate nucleus in AD patients. Zubenko et al., *Biol. Psych.* (1986) 21:1365-1381, found a correlation between the severity of AD with levels of ACE in CSF. Whether the alterations in ACE are causative in the progression of dementia or correlates of the disease progress is not known.

Recent evidence that inhibition of ACE can have a modulatory effect on learning and memory was reported by Usinger et al. *Drug Dev. Research* (1988) 14:315-324 (also European Patent Application EP 307,872 to Hoechst, published Mar. 22, 1989. These authors investigated the effects of the ACE inhibitor Hoe 288 on: uphill avoidance in mice, scopolamine-induced (muscarinic receptor blocker) amnesia of a PA response, and a scopolamine-induced impairment of eight arm radial maze performance in rats. In the uphill avoidance test, an acute administration of Hoe 288 at 30 mg/kg PO improved performance during retention testing. In the scopolamine-induced PA amnesia, administration of Hoe 288 three times per day at 1, 3 and 10 mg/kg PO, partially reversed the amnesia. Finally, 3 mg/kg IP partially antagonized the effects of muscarinic receptor blockade or performance. Further, these authors demonstrated that acute or repeated administration of the ACE inhibitor induced a significant decrease in ACh in the striatum and hypothalamus.

Similar results were reported by Costall et al., *Pharmacol, Biochem, Behav.* (1989) 33:573-579, using the ACE inhibitor captopril. These authors demonstrated that the subchronic treatment with captopril increased the rate of acquisition of light/dark habituation performance. Further, anticholinergic scopolamine-induced disruption of performance in this test model was prevented by daily treatment with captopril.

The ACE inhibitor SQ 29852 has also been reported to provide protective effects on memory of previously learned tasks and to ameliorate, at least in part, an anticholinergic effect on performance (European Patent Application EP 288,907 to Squibb, published Nov. 2, 1988).

Evidence for a role of AII on cholinergic function was also reported by Barnes et al. (*Brain Research* (1989) 491:136-143), who examined the affect of AII on an in vitro model of potassium stimulated release of [3H]ACh. AII, but not AI, reduced potassium-stimulated release of ACh without effects on basal levels. This effect was antagonized by the AII antagonist [1-sarcosine, 8-threonine]angiotensin II. These results suggest that AII can inhibit the release of ACh in entorhinal cortex from rat brain.

The results summarized above suggest that increased AII activity in brain may maintain inhibitory control of cholinergic neurons, resulting in impaired cognitive performance.

SUMMARY OF THE INVENTION

According to the present invention there is provided a method of treating central nervous system (CNS) disorders, such as cognitive and learning disorders, mediated by AII in a mammal comprising administering to the mammal a pharmaceutical composition comprising a compound having the formula (I):

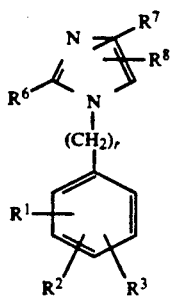

wherein:
$R^1$ is $4\text{-}CO_2H$; $4\text{-}CO_2R^9$;

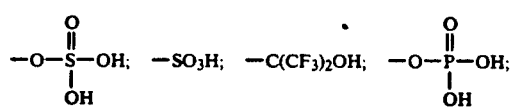

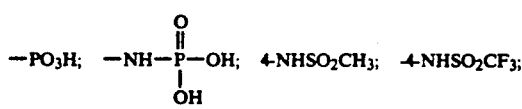

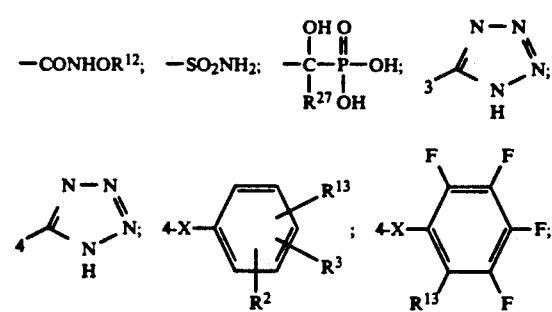

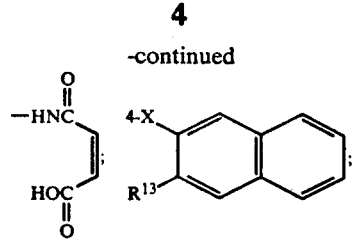

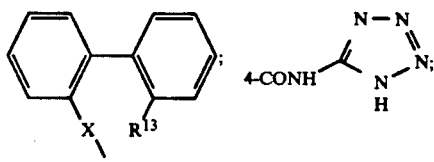

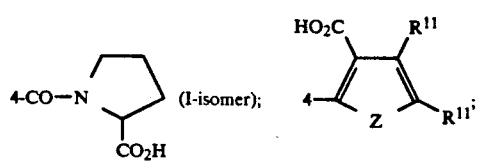

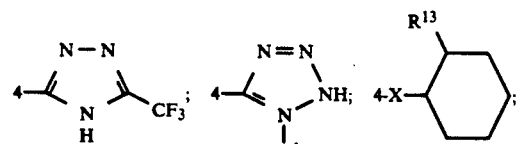

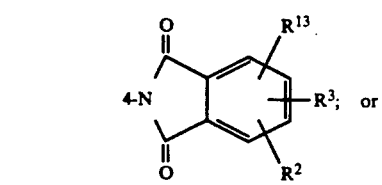

$R^2$ is H; Cl; Br; I; F; $NO_2$; CN; alkyl of 1 to 4 carbon atoms; acyloxy of 1 to 4 carbon atoms; alkoxy of 1 to 4 carbon atoms; $CO_2H$; $CO_2R^9$; $NHSO_2CH_3$; $NHSO_2CF_3$; $CONHOR^{12}$; $SO_2NH_2$;

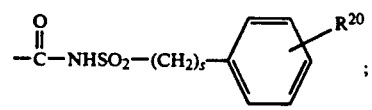

aryl; or furyl;

$R^3$ is H; Cl, Br, I or F; alkyl of 1 to 4 carbon atoms or alkoxy of 1 to 4 carbon atoms;

$R^4$ is CN, $NO_2$ or $CO_2R^{11}$;

$R^5$ is H, alkyl of 1 to 6 carbon atoms, cycloalkyl of 3 to 6 carbon atoms, alkenyl or alkynyl of 2 to 4 carbon atoms;

$R^6$ is alkyl of 2 to 10 carbon atoms, alkenyl or alkynyl of 3 to 10 carbon atoms or the same groups substituted with F or $CO_2R^{14}$; cycloalkyl of 3 to 8 carbon atoms, cycloalkylalkyl of 4 to 10 carbon atoms; cycloalkylalkenyl or cycloalkylalkynyl of 5 to 10 carbon atoms; $(CH_2)_sZ(CH_2)_mR^5$ optionally substituted with F or $CO_2R^{14}$; benzyl or benzyl substituted on the phenyl ring with 1 or 2 halogens, alkoxy of 1 to 4 carbon atoms, alkyl of 1 to 4 carbon atoms or nitro;

$R^7$ is H, F, Cl, Br, I, $NO_2$, $C_vF_{2v+1}$, where v=1-6; $C_6F_5$; CN;

straight or branched alkyl of 1 to 6 carbon atoms; phenyl or phenylalkyl, where alkyl is 1 to 3 carbon atoms; or substituted phenyl or substituted phenylalkyl, where alkyl is 1 to 3 carbon atoms, substituted with one or two substituents selected from alkyl of 1 to 4 carbon atoms, F, Cl, Br, OH, $OCH_3$, $CF_3$, and COOR, where R is H, alkyl of 1 to 4 carbon atoms, or phenyl; vinyl; alkynyl of 2-10 carbon atoms; phenylalkynyl where the alkynyl portion is 2-6 carbon atoms; heteroaryl selected from 2- and 3-thienyl, 2- and 3-furyl, 2-, 3-, and 4-pyridyl, 2-pyrazinyl, 2-, 4-, and 5-pyrimidinyl, 3- and 4-pyridazinyl, 2-, 4- and 5-thiazolyl, 2-, 4-, and 5-selenazolyl, 2-, 4-, and 5-oxazolyl; 2- or 3-pyrrolyl, 3-, 4- or 5-pyrazolyl, and 2-, 4- or 5-imidazolyl; o-, m- or p-biphenylyl; o-, m- or p-phenoxyphenyl; substituted phenylalkynyl, heteroaryl, biphenylyl or phenoxphenyl as defined above substituted on ring carbon with 1 or 2 substituents selected from halogen, alkoxy of 1-5 carbon atoms, alkyl of 1-5 carbon atoms, $-NO_2$, $-CN$, $-CF_3$, $-COR^{16}$, $-CH_2OR^{17}$, $-NHCOR^{17}$, $CONR^{18}R^{19}$, $S(O)_rR^{17}$, and $SO_2NR^{18}R^{19}$; pyrollyl, pyrazolyl or imidazolyl as defined above substituted on ring nitrogen with alyl of 1-5 carbon atoms or benzyl; or substituted alkyl, alkenyl, or alkynyl of 1 to 10 carbon atoms substituted with a substituted or unsubstituted heteroaryl, biphenylyl or phenoxyphenyl group as defined above; 1- or 2- naphthyl; 5- or 6-naphthoquinonyl; 3-, 4-, or 5-acenaphtyl; 3-, 4-, or 5-acenaphthenyl; 1-, 2- or 9-anthracenyl; 1- or 2-anthraquinonyl; 1-, 2-, 3-, 4-, or 9-phenanthrenyl; 2-, 3-, 4-, 5-, 6-, 7- or 8-quinolinyl; 1-, 3-, 4-, 5-, 6-, 7- or 8-isoquinonyl; 2-, 3-, 4-, 5-, 6- or 7-indolyl which can be substituted on ring nitrogen with lower alkyl of 1 to 5 carbon atoms or benzyl; 4-, 5-, 6- or 7-indenyl; 2-, 3-, 4-, 5-, 6- or 7-benzofuryl; 2-, 3-, 4-, 5-, 6- or 7-benzothienyl; 1-, 2-, 3- or 4-dibenzofuryl; 1-, 2-, 3- or 4-dibenzothienyl; 1-, 2-, 3- or 4-fluoenyl; any of the foregoing polycyclic aryl groups substituted with 1 or 2 substituents selected from halogen, alkoxy of 1-5 carbon atoms, alkyl of 1-5 carbon atoms, $-NO_2$, $-CN$, $-CF_3$, $-COR^{16}$, $-CH_2OR^{17}$, $-NHCOR^{17}$, $CONR^{18}R^{19}$, $S(O)_rR^{17}$, and $SO_2NR^{18}R^{19}$; the anhydride of 4,5-dicarboxyl-1- or 2-naphthyl; or substituted alkyl of 1 to 10 carbon atoms, alkenyl or alkynyl of 2 to 10 carbon atoms substituted with a substituted or unsubstituted polycyclic aryl group as defined above;

$R^8$ is H, CN, alkyl of 1 to 10 carbon atoms, alkenyl of 3 to 10 carbon atoms, or the same groups substituted with F; phenylalkenyl wherein the aliphatic portion is 2 to 6 carbon atoms; $-(CH_2)_m$-imidazol-1-yl; $-(CH_2)_m$-1,2,3-triazolyl optionally substituted with one or two groups selected from $CO_2CH_3$ or alkyl of 1 to 4 carbon atoms; $-(CH_2)_s$-tetrazolyl;

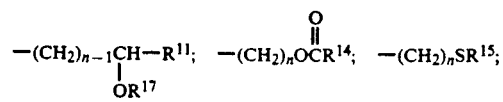
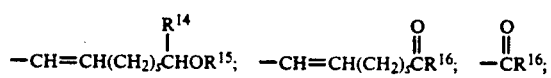
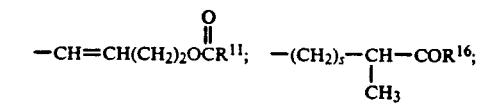
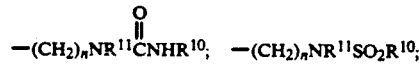
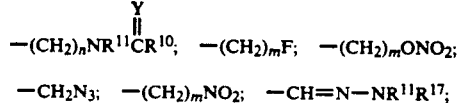
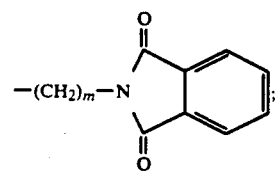
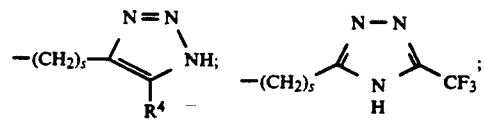
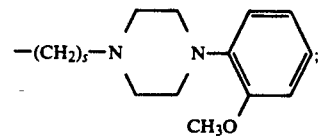
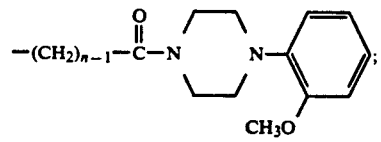
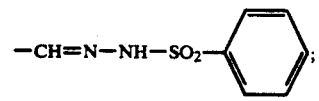
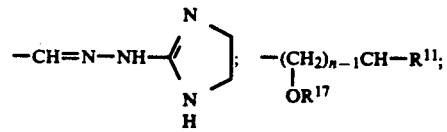
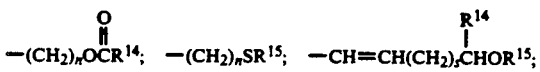
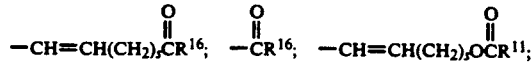

-continued

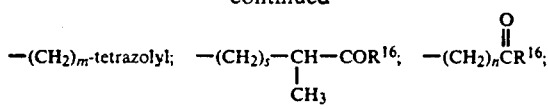

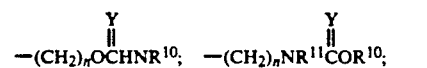

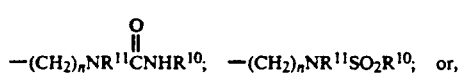

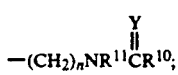

$R^9$ is;

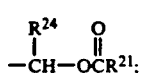

$R^{10}$ is alkyl of 1 to 6 carbon atoms or perfluoroalkyl of 1 to 6 carbon atoms, 1-adamantyl, 1-naphthyl, 1-(1-naphthyl)ethyl, or $(CH_2)_pC_6H_5$;

$R^{11}$ is H, alkyl of 1 to 6 carbon atoms, cycloalkyl of 3 to 6 carbon atoms, phenyl or benzyl;

$R^{12}$ is H, methyl or benzyl;

$R^{13}$ is $-CO_2H$; $-CO_2R^9$; $-CH_2CO_2H$, $-CH_2CO_2R^9$;

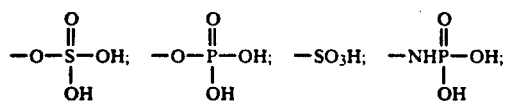

$-PO_3H$; $-C(CF_3)_2OH$; $-NHSO_2CH_3$; $-NHSO_2CF_3$; $-NHCOCF_3$; $-CONHOR^{12}$; $-SO_2NH_2$;

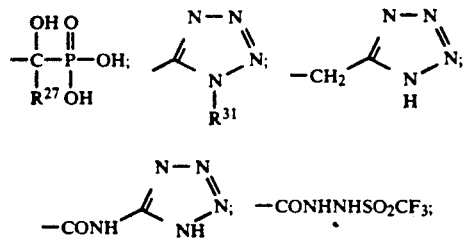

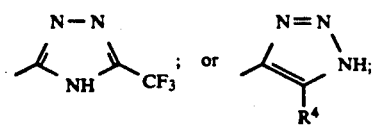

$R^{14}$ is H, alkyl or perfluoroalkyl of 1 to 8 carbon atoms, cycloalkyl of 3 to 6 carbon atoms, phenyl or benzyl;

$R^{15}$ is H, alkyl of 1 to 6 carbon atoms, cycloalkyl of 3 to 6 carbon atoms, phenyl, benzyl, acyl of 1 to 4 carbon atoms, phenacyl;

$R^{16}$ is H, alkyl of 1 to 6 carbon atoms, cycloalkyl of 3 to 6 carbon atoms, $(CH_2)_pC_6H_5$, $OR^{17}$, or $NR^{18}R^{19}$;

$R^{17}$ is H, alkyl of 1 to 6 carbon atoms, cycloalkyl of 3 to 6 carbon atoms, phenyl or benzyl;

$R^{18}$ and $R^{19}$ independently are H, alkyl of 1 to 4 carbon atoms, phenyl, benzyl, a-methylbenzyl, or taken together with the nitrogen form a ring of the formula

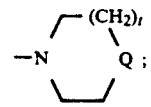

Q is $NR^{20}$, O or $CH_2$;

$R^{20}$ is H, alkyl of 1–4 carbon atoms, or phenyl;

$R^{21}$ is alkyl of 1 to 6 carbon atoms, $-NR^{22}R^{23}$, or

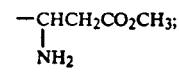

$R^{22}$ and $R^{23}$ independently are H, alkyl of 1 to 6 carbon atoms, benzyl, or are taken together as $(CH_2)_u$ where u is 3–6;

$R^{24}$ is H, $CH_3$ or $-C_6H_5$;

$R^{25}$ is $NR^{27}R^{28}$, $OR^{28}$, $NHCONH_2$, $NHCSNH_2$,

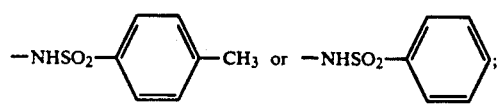

$R^{26}$ is hydrogen, alkyl with from 1 to 6 carbon atoms, benzyl, or allyl;

$R^{27}$ and $R^{28}$ are independently hydrogen, alkyl with from 1 to 5 carbon atoms, or phenyl;

$R^{29}$ and $R^{30}$ are independently alkyl of 1–4 carbon atoms or taken together are $-(CH_2)_q-$;

$R^{31}$ is H, alkyl of 1 to 4 carbon atoms, $-CH_2CH=CH_2$ or $-CH_2C_6H_4R^{32}$;

$R^{32}$ is H, $NO_2$, $NH_2$, OH or $OCH_3$;

X is a carbon-carbon single bond, $-CO-$, $-CH_2-$, $-O-$, $-S-$, $-NH-$,

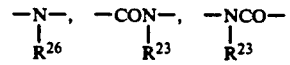

$-OCH_2-$, $-CH_2O-$, $-SCH_2-$, $-CH_2S-$, $NHC(R^{27})(R^{28})$, $-NR^{23}SO_2-$, $-SO_2NR^{23}-$, $-C(R^{27})(R^{28})NH-$, $-CH=CH-$, $-CF=CF-$, $-CH=CF-$, $-CF=CH-$, $-CH_2CH_2-$, $-CF_2CF_2-$,

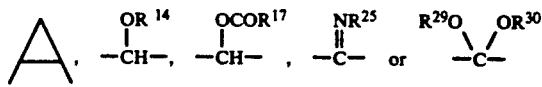

Y is O or S;
Z is O, $NR^{11}$, or S;
m is 1 to 5;
n is 1 to 10;
p is 0 to 3;
q is 2 to 3;
r is 0 to 2;
s is 0 to 5;
t is 0 to 1;
and pharmaceutically acceptable salts of these compounds; provided that:
(1) the $R^1$ group is not in the ortho position;
(2) when $R^1$ is

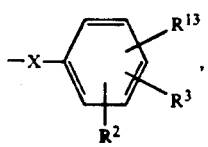

X is a single bond, and $R^{13}$ is $CO_2H$, or

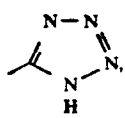

then $R^{13}$ must be in the ortho or meta position; or when $R^1$ and X are as above and $R^{13}$ is $NHSO_2CF_3$ or $NHSO_2CH_3$, $R^{13}$ must be ortho;

(3) when $R^1$ is

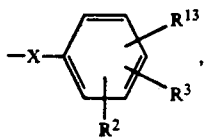

and X is other than a single bond, then $R^{13}$ must be ortho except when $X=NR^{23}CO$ and $R^{13}$ is $NHSO_2CF_3$ or $NHSO_2CH_3$, then $R^{13}$ must b eortho or meta;

(4) when $R^1$ is $4-CO_2H$ or a salt thereof, $R^6$ cannot be S-alkyl;

(5) when $R^1$ is $4-CO_2H$ or a salt thereof, the substituent on the 4-position of the imidazole cannot be $CH_2OH$, $CH_2OCOCH_3$, or $CH_2CO_2H$;

(6) when $R^1$ is

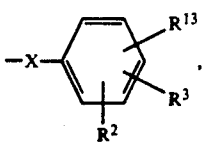

X is $-OCH_2-$, and $R^{13}$ is $2-CO_2H$, and $R^7$ is H then $R^6$ is not $C_2H_5S$;

(7) when $R^1$ is

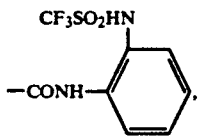

and $R^6$ is n-hexyl, then $R^7$ and $R^8$ are not both hydrogen;

(8) when $R^1$ is

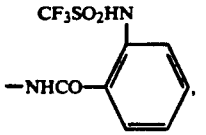

$R^6$ is not methoxybenzyl;

(9) the $R^6$ group is not $-F-CHCH_2CH_2CH_3$ or $CH_2OH$;

(10) when r=O, $R^1$ is

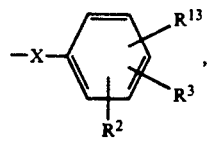

X is $-NH-C=O$, $R^{13}$ is $2-NHSO_2CF_3$, and $R^6$ is n-propyl, then $R^7$ and $R^8$ are not $-CO_2CH_3$;

(11) when r=O, $R^1$ is

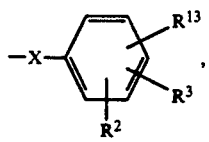

X is $NH-C=O$, $R^{13}$ is 2-COOH, and $R^6$ is n-propyl, then $R^7$ and $R^8$ are not $-CO_2CH_3$;

(12) when r=1, $R^1=$

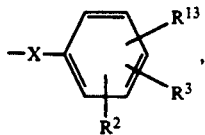

X is a single bond, $R^7$ is Cl, and $R^8$ is $-CHO$, then $R^{13}$ is not 3-(tetrazol-5-yl);

(13) when r=1, $R^1=$

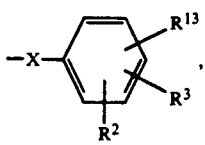

X is a single bond, $R^7$ is Cl, and $R^8$ is $-CHO$, then $R^{13}$ is not 4-(tetrazol-5-yl).

Preferred in the method of this invention are compounds having the formula (II):

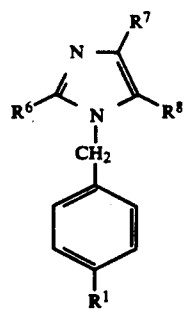

(II)

wherein $R^1$ is $-CO_2H$; $-NHSO_2CF_3$;

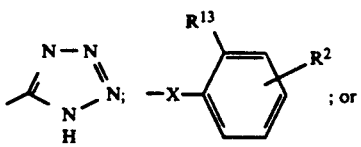

; or

-continued

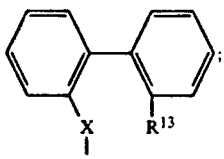

R⁶ is alkyl of 3 to 10 carbon atoms, alkenyl of 3 to 10 carbon atoms, alkynyl of 3 to 10 carbon atoms, cycloalkyl of 3 to 8 carbon atoms, benzyl substituted on the phenyl ring with up to two groups selected from alkoxy of 1 to 4 carbon atoms, halogen, alkyl of 1 to 4 carbon atoms, and nitro;

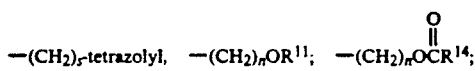

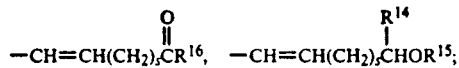

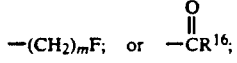

phenylalkenyl wherein the aliphatic portion is 2 to 4 carbon atoms; —(CH₂)$_m$-imidazol-1-yl; or —(CH₂)$_m$-1,2,3-triazolyl optionally substituted with one or two groups selected from —CO₂CH₃ or alkyl of 1 to 4 carbon atoms;

R¹³ is —CO₂H, —CO₂R⁹, NHSO₂CF₃; SO₃H; or

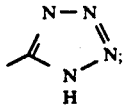

R¹⁶ is H, alkyl of 1 to 5 carbon atoms, OR¹⁷, or NR¹⁸R¹⁹;

X is carbon—carbon single bond, —CO—, CH₂CH₂—,

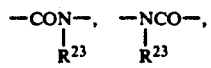

—OCH₂—, —CH₂O—, —O—, —SCH₂—, —CH₂S—, —NH—CH₂—, —CH₂NH— or —CH=CH—; and pharmaceutically acceptable salts of these compounds.

More preferred in the process of the invention are compounds of the preferred scope where:

R² is H, alkyl of 1 to 4 carbon atoms, halogen, or alkoxy of 1 to 4 carbon atoms;

R⁶ is alkyl, alkenyl or alkynyl of 3 to 7 carbon atoms;

R⁷ is heteroaryl selected from 2- and 3-thienyl, 2- and 3-furyl, 2-, 3-, and 4-pyridyl, p-biphenylyl; H, Cl, Br, I; C$_v$F$_{2v+1}$, where v=1–3;

straight or branched chain alkyl of 1 to 6 carbon atoms; or phenyl;

R⁸ is

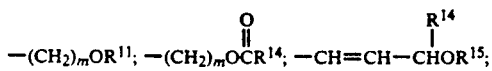

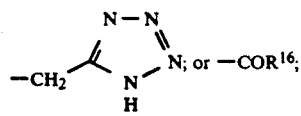

R¹⁰ is CF₃, alkyl of 1 to 6 carbon atoms or phenyl;
R¹¹ is H, or alkyl of 1 to 4 carbon atoms;
R¹³ is CO₂H; CO₂CH₂OCOC(CH₃)₃; NHSO₂CF₃;

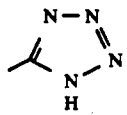

R¹⁴ is H, or alkyl of 1 to 4 carbon atoms;
R¹⁵ is H, alkyl of 1 to 4 carbon atoms, or acyl of 1 to 4 carbon atoms;
R¹⁶ is H, alkyl of 1 to 5 carbon atoms; OR¹⁷; or

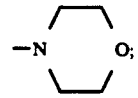

m is 1 to 5;

X=single bond, —O—; —CO—; —NHCO—; or —OCH₂—; and pharmaceutically acceptable salts.

More preferred in the method of the invention are compounds of Formula II, wherein R¹ is

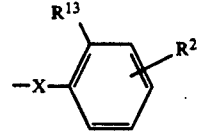

and X is a single bond; and pharmaceutically suitable salts thereof.

Most preferred in the method of the invention are compounds of formula II selected from the following, and pharmaceutically acceptable salts thereof.

2-Butyl-4-chloro-1-[(2'-(1H-tetrazol-5-yl)biphenyl-4-yl)methyl]-5-(hydroxymethyl)imidazole.

2-Butyl-4-chloro-1-[(2'-carboxybiphenyl-4-yl)-methyl]-5-(hydroxymethyl)imidazole.

2-Butyl-4-chloro-1-[(2'-carboxybiphenyl-4-yl)-methyl]-5-[(methoxycarbonyl)aminomethyl] imidazole.

2-Butyl-4-chloro-1-[(2'-carboxybiphenyl-4-yl) -methyl]-5-[(propoxycarbonyl)aminomethyl] imidazole.

2-Butyl-4-chloro-1-[(2'-carboxybiphenyl-4-yl) methyl]imidazole-5-carboxaldehyde.

2-Butyl-1-[(2'-carboxybiphenyl-4-yl)methyl]-imidazole-5-carboxaldehyde.

2-(1E-Butenyl)-4-chloro-1-[(2'-carboxybiphenyl -4-yl)methyl]-5-(hydroxymethyl)imidazole.

2-(1E-Butenyl)-4-chloro-1-[(2'-carboxybiphenyl -4-yl)methyl]imidazole-5-carboxaldehyde.
2-Propyl-4-chloro-1-[(2'-(1H-tetrazol-5-yl)biphenyl-4-yl)methyl]-5-(hydroxymethyl) imidazole.
2-Propyl-4-chloro-1-[(2'-(1H-tetrazol-5-yl)biphenyl-4-yl)methyl]imidazole-5-carboxaldehyde.
2-Butyl-4-chloro-1-[2'-(1H-tetrazol-5-yl)biphenyl-4-yl)methyl]imidazole-5-carboxaldehyde.
2-(1E-Butenyl)-4-chloro-1-[(2'-(1H-tetrazol-5-yl)biphenyl-4-yl)methyl]-5-hydroxymethyl)imidazole.
2-(1E-Butenyl)-4-chloro-1-[(2'-(1H-tetrazol-5-yl)biphenyl-4-yl)methyl]imidazole-5-carboxaldehyde.
2-Butyl-4-chloro-1-[(2'-(1H-tetrazol-5-yl) -biphenyl-4-yl)methyl]imidazole-5-carboxylic acid.
2-Propyl-4-chloro-1-[(2'-(1H-tetrazol-5-yl) -biphenyl-4-yl)methyl]imidazole-5-carboxylic acid.
2-Propyl-4-trifluoromethyl-1-[(2'-(1H -tetrazol-5-yl)biphenyl-4-yl)methyl]imidazole-5-carboxylic acid.
2-Propyl-4-trifluoromethyl-1-[(2'-(1H -tetrazol-5-yl)biphenyl-4-yl)methyl]-5-(hydroxylmethyl) -imidazole.
2-Butyl-4-trifluoromethyl-1-[(2'-(1H-tetrazol-5-yl)biphenyl-4-yl)methyl]imidazole-5-carboyxlic acid.
2-Propyl-4-trifluoromethyl-1-[(2'-(carboxybiphenyl-4-yl)methyl]imidazole-5-carboxaldehyde.
2-Propyl-4-pentafluoroethyl-1-[(2'-(1H -tetrazol-5-yl)biphenyl-4-yl)methyl]-5-(hydroxymethyl) -imidazole.
2-Propyl-4-pentafluoroethyl-1-[(2'-(1H-tetrazol -5-yl)biphenyl-4-yl)methyl]imidazole-5-carboxylic acid.
2-Propyl-4-pentafluoroethyl-[(2'-(1H-tetrazol -5-yl)biphenyl-4-yl)methyl]imidazole-5-carboxaldehyde.
1-[(2'-(1H-Tetrazol-5-yl)biphenyl-4-yl)methyl]-4-phenyl-2-propylimidazole-5-carboxaldehyde
1-[(2'-Carboxybiphenyl-4-yl)methyl]-4-phenyl-2-propylimidazole-5-carboxaldehyde Note that throughout the text when an alkyl substituent is mentioned, the normal alkyl structure is meant (i.e., butyl is n-butyl) unless otherwise specified.

Pharmaceutically suitable salts include both the metallic (inorganic) salts and organic salts; a list of which is given in *Remington's Pharmaceutical Sciences*, 17th Edition, pg. 1418 (1985). It is well known to one skilled in the art that an appropriate salt form is chosen based on physical and chemical stability, flowability, hydroscopicity and solubility. Prefered salts of this invention for the reasons cited above include potassium, sodium, calcium and ammonium salts.

Also within the scope of this invention are methods of using pharmaceutical compositions comprising a suitable pharmaceutical carrier and a compound of Formula (I), to treat CNS disorders. The pharmaceutical compositions can optionally contain one or more other therapeutic agents.

It should be noted in the foregoing structural formula, when a radical can be a substituent in more than one previously defined radical, that first radical can be selected independently in each previously defined radical. For example, $R^1$, $R^2$ and $R^3$ can each be CONHOR$^{12}$. $R^{12}$ need not be the same substituent in each of $R^1$, $R^2$ and $R^3$ but can be selected independently for each of them.

DETAILED DESCRIPTION OF THE INVENTION

The compounds of Formula (I) useful in this invention are described in and prepared by methods set forth in European Patent Application EPA 0 324 377, published 7/19/89, (page 17, line 5 through page 212, line 32), copending commonly-assigned U.S. patent application U.S. Ser. No. 07/375,069, filed Jun. 30, 1989, (page 16, line 21 through page 133, line 35), and copending commonly-assigned U.S. patent application U.S. Ser. No. 07/373,755, filed Jun. 30, 1989, (page 16, line 21 through page 153, line 15), the disclosures of which are hereby incorporated by reference Two distinct angiotensin II (AII) receptor subtypes have been discovered and characterized by means of the discriminatory effect of dithiothreitol (DTT) and by two structurally dissimilar nonpeptide AII receptor antagonists, denoted as DuP 753 and EXP655, which show reciprocal selectivity for the two subtypes (Chiu et al., *Biochem. and Biophys. Res. Comm.* (1989)165:196–203). DuP 753 is 2-n -butyl-4-chloro-5-hydroxymethyl-1-[(2'-(1H-tetrazol-5-yl)biphenyl-4-yl)methyl]-imidazole (Example 89 of European Published Application EPA 0 324 377). EXP655 is 1-(4-amino -3-methylphenyl)methyl-5-diphenylacetyl-4,5,6,7-tetrahydro -1H-imidazo[4,5-c]pyridine-6-carboxylic acid (Example 13 of EPA 0 245 637).

Using radioligand-receptor binding techniques, DuP 753 was found to be highly specific for an AII receptor site, designated AII receptor subtype-1 or AII-1, displaying an inhibitory constant IC$_{50}$ value of about $1.2 \times 10^{-8}$ M in rat adrenal cortex. This type of AII receptor was particularly sensitive to inactivation by DTT. EXP655 exhibited very low affinity for the AII-1 site (IC$_{50}$ value of about $3.0 \times 10^{-4}$ M), but was highly selective for a distinct AII receptor site, designated AII receptor subtype-2 or AII-2, exhibiting an inhibitory constant IC$_{50}$ value of about $1.0 \times 10^{-7}$ M in rat adrenal cortex. In contrast to the AII-1 receptor, the AII-2 receptor was resistant to DTT inactivation. Moreover, DuP 753 had very low affinity for the AII-2 receptor (IC$_{50}$ of about $1.4 \times 10^{-4}$ M).

The rat adrenal medulla contains a relatively high density of AII receptors which are predominately the AII-2 subtype, as reported in the Chiu et al. paper.

Whitebread et al., *Biochem. and Biophys, Res. Comm.* (1989) 163:284–291, also reports the discovery of two AII receptor subtypes.

The compounds of Formula (I) above (which includes DuP 753) block the AII-1 receptor subtype. Compounds of Formula (I) above wherein $R^7$ or $R^8$ at the 4-position on the imidazole ring is phenyl, phenylalkyl, phenylalkenyl, phenylalkynyl, substituted phenyl, substituted phenylalkyl, substituted phenylalkenyl or substituted phenylalkynyl, block both the AII-1 and the AII-2 receptor subtypes. For example, Compounds A and B identified below show affinity for both AII-1 and AII-2 receptors in the tests described in the Chiu et al. paper. Compound A (Example 324A of EPA 0 324 377) is 1-[(2'-(1H tetrazol-5-yl)biphenyl-4-yl)methyl]-4-phenyl-2-propylimidazole-5-carboxaldehyde. Compound B (Example 322 of EPA 0 324 377) is 1-[(2'-carboxybiphenyl-4-yl)methyl]-4-phenyl-2-propylimidazole-5-carboxaldehyde. The results obtained in the tests for receptor specificity are summarized in Table 1:

TABLE 1

| Antagonist Specificity Exhibited by AII Receptor Subtypes IC$_{50}$ (M) | | |
|---|---|---|
| Compound | AII-1 | AII-2 |
| AII | $1.5 \times 10^{-9}$ | $0.6 \times 10^{-9}$ |
| Saralasin | $0.7 \times 10^{-9}$ | $0.3 \times 10^{-9}$ |

TABLE 1-continued

Antagonist Specificity Exhibited by All Receptor Subtypes
$IC_{50}$ (M)

| Compound | AII-1 | AII-2 |
|---|---|---|
| DuP 753 | $1.9 \times 10^{-8}$ | $5.8 \times 10^{-5}$ |
| EXP655 | $3.0 \times 10^{-4}$ | $2.8 \times 10^{-8}$ |
| Compound A | $2.2 \times 10^{-8}$ | $2.4 \times 10^{-6}$ |
| Compound B | $2.9 \times 10^{-7}$ | $4.3 \times 10^{-6}$ |

AII-1 site binding was determined using adrenal cortex microsomes in the presence of $10^{-5}$ M EXP655. AII-2 site binding was determined using adrenal medulla microsomes in the presence of $10^{-5}$ M DuP 753. $IC_{50}$ was determined by displacement of [$^{125}$I]AII from the receptor by the indicated compound.

Using procedures described by Bennett and Snyder (1976) *J. Biol. Chem.* 254:7423–7430, we have discovered that the rat brain also contains a high density of AII receptors which are predominately the AII-2 subtype. EXP655 displaced the [$^{125}$I]AII binding in rat brain membranes in a concentration-dependent manner yielding $IC_{50}$ value of $3.2 \times 10^{-7}$ M. In contrast, DuP 753 displaced the binding of AII inefficiently, with an $IC_{50}$ value of $1.5 \times 10^{-4}$ M.

The distribution of AII-1 and AII-2 receptors in certain regions of the brain was determined by the binding of AII antagonists to different sections of brain slices. The results indicate that there are clusters of DTT-sensitive, DUP 753-sensitive AII binding sites (AII-1 receptors) in the brain; however, the majority of binding sites in the brain are DTT-insensitive and EXP655-sensitive, corresponding to AII-2 receptors.

Despite a high density of AII-2 binding sites in the brain, AII-1 receptor antagonists prevent amnesia induced by renin, as shown by the results in the renin-disrupted passive avoidance retention test described below. These results indicate that AII-1 receptor antagonists, such as the compounds of Formula (I), are useful for treatment of CNS disorders, such as learning disorders, cognitive disfunction, schizophrenic polydipsia, centrally induced hypertension, diabetic nephropathy, and excessive milk production. Compound C is the sodium salt of 2-n-propyl-1-[(2'-(1H-tetrazol-5-yl)biphenyl-4-yl)methyl]-4-trifluoromethylimidazole-5-carboxylic acid (Example 265A of EPA 0 324 377). Compound D is the sodium salt of 2-n-propyl-5-hydroxymethyl-1-[(2'-(1H-tetrazol-5-yl)biphenyl-4-yl)methyl]-4-trifluoromethylimidazole (Example 124D of EPA 0 324 377). Both Compounds C and D are AII-1 receptor antagonists.

RENIN-DISRUPTED PASSIVE AVOIDANCE RETENTION

Experimentally naive male Sprague-Dawley rats 100 to 125 days oil (Charles River Breeding Laboratories, Kingston, N.Y.), weighing between 175 to 200 gm were used. The animals were housed four per cage ($45.0L \times 20.0H \times 26.0W$ cm) with free access to food and water. They were maintained on a 12 h light/dark cycle (lights on 0600 h) and at a room temperature of $22 \pm 1°$ C. with relative humidity of $50 \pm 10\%$.

The experimental sessions were conducted in a two-compartment passive avoidance box. One compartment, made of clear plastic with a perforated clear plastic floor, measured $21(L) \times 24.5(H) \times 17(W)$ cm and was illuminated with a 60 watt incandescent light bulb placed 36 cm above the floor. The other compartment, made of black plastic, measured 30.5 (L) $\times$ 20.3 (H) $\times$ 21.5 (W) cm with a floor made of 4 mm stainless steel rods spaced 1.2 cm apart. A grid floor shocker (Coulbourn Instruments) was connected to the steel rods and provided scrambled footshock. The two compartments were separated by a solenoid-operated slide door (Lafayette Instrument Co., Lafayette, Ind.). An electronic counter (Coulbourn Instruments), triggered by the opening or closing of the slide door, recorded acquisition and retention latencies (latencies were defined as the time it took an animal to enter the dark compartment).

Passive avoidance training began by placing the rat into the clear compartment of the two-compartment passive avoidance box. Following a 10 sec delay, the slide door to the dark compartment was raised. Once the rat moved completely into the dark compartment (all four paws on the shock grid floor) the slide door was lowered, and after a 10 sec. delay, a 1.0 mA shock was applied to the grid floor for three sec. A second three s shock was delivered after an additional 10 sec delay. The rats were immediately removed from the dark compartment and returned to their home cage. A retention test was given 24 h later. It proceeded in the same manner as the training session except that no shock was applied to the grid floor when the rats were provided access to the dark compartment for a maximum of 300 sec.

Renin at 0.1 to 5 $\mu g/5$ $\mu L$ (Sigma Chemicals), and EXP655 at 0.1–100 $\mu g/5$ $\mu L$ were dissolved in 0.85% saline solution. All drugs were administered IVT 60 minutes prior to acquisition training in a volume of 5 $\mu l$. Doses are expressed as the free base weight of each compound.

Renin injected IVT produces a reliable memory deficit in rats (Table 2). Two AII-1 receptor antagonists, Compounds C and D, when co-administered with renin protected against the amnesia (Tables 3 and 4). EXP655, an AII-2-specific antagonist, was much less effective in preventing the amnesia (Table 5).

TABLE 2

Renin-induced Disruption of Passive Avoidance Retention

| [renin], ($\mu g/5$ $\mu L$ IVT) | Median Retention Latency, (sec) |
|---|---|
| 0 | 300 |
| 0.1 | 254 |
| 0.5 | 117 |
| 1.0 | 27 |
| 3.0 | 56.5 |
| 5.0 | 17 |

TABLE 3

Compound C Blocks Renin-induced Disruption of Passive Avoidance Retention

| [renin], ($\mu g/5$ $\mu L$ IVT) | [Example 5], ($\mu g/5$ $\mu L$ IVT) | Median Retention Latency, (sec) |
|---|---|---|
| 0 | 0 | 300 |
| 1.0 | 0 | 48 |
| 1.0 | 10 | 264 |
| 1.0 | 30 | 300 |
| 1.0 | 100 | 34.5 |

TABLE 4

Compound D Blocks Renin-induced Disruption of Passive Avoidance Retention

| [renin], ($\mu g/5$ $\mu L$ IVT) | [Example 6], ($\mu g/5$ $\mu L$ IVT) | Median Retention Latency, (sec) |
|---|---|---|
| 0 | 0 | 300 |

TABLE 4-continued

Compound D Blocks Renin-induced
Disruption of Passive Avoidance Retention

| [renin], ($\mu$g/5 $\mu$L IVT) | [Example 6], ($\mu$g/5 $\mu$L IVT) | Median Retention Latency, (sec) |
|---|---|---|
| 1.0 | 0 | 32 |
| 1.0 | 30 | 242 |
| 1.0 | 100 | 10 |

TABLE 5

Effects of EXP655 On Renin-induced
Disruption of Passive Avoidance Retention

| [renin], ($\mu$g/5 $\mu$L IVT) | [Example 2], ($\mu$g/5 $\mu$L IVT) | Median Retention Latency, (sec) |
|---|---|---|
| 0 | 0 | 300 |
| 1.0 | 0 | 15.5 |
| 1.0 | 0.1 | 19 |
| 1.0 | 0.3 | 22 |
| 1.0 | 1.0 | 15 |
| 1.0 | 3.0 | 29 |
| 1.0 | 10 | 15 |
| 1.0 | 30 | 67 |
| 1.0 | 100 | 16 |

DOSAGE FORMS

The compounds of this invention can be administered for the treatment of AII-mediated CNS disorders according to the invention by any means that effects contact of the active ingredient compound with the site of action, i.e., the CNS, in the body of a warm-blooded animal. For example, administration can be parenteral, i.e., subcutaneous, intravenous, intramuscular, or intra peritoneal. Alternatively, or concurrently, in some cases administration can be by the oral route.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

For the purpose of this disclosure, a warm-blooded animal is a member of the animal kingdom possessed of a homeostatic mechanism and includes mammals and birds.

The dosage administered will be dependent on the age, health and weight of the recipient, the extent of disease, kind of concurrent treatment, if any, frequency of treatment and the nature of the effect desired. Usually, a daily dosage of active ingredient compound will be from about 1-500 milligrams per day. Ordinarily, from 10 to 100 milligrams per day in one or more applications is effective to obtain desired results.

The active ingredient can be administered orally in solid dosage forms, such as capsules, tablets, and powders, or in liquid dosage forms, such as elixirs syrups, and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in Remington's Pharmaceutical Sciences, A. Osol, a standard reference text in this field.

Useful pharmaceutical dosage-forms for administration of the compounds of this invention can be illustrated as follows:

Capsules:

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules:

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

Tablets:

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable:

A parenteral composition suitable for administration by injection is prepared by stirring 1.5% by weight of active ingredient in 10% by volume propylene glycol. The solution is made to volume with water for injection and sterilized.

Suspension:

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise in conjunction with another therapeutic agent. When the drugs are administered in physical combination, the dosage form and administration route should be selected for compatibility with both drugs.

We claim:

1. A method of treating impaired cognitive performance which comprises administering to a patient in need of such treatment an effective amount of a compound of formula II.

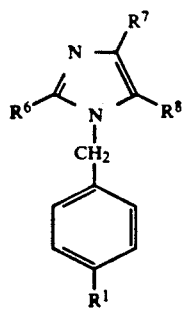

wherein
$R^1$ is —CO$_2$H; —NHSO$_2$CF$_3$;

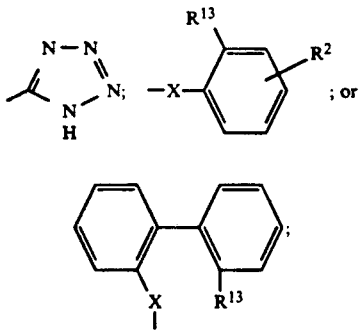

$R^2$ is H, alkyl of 1 to 4 carbon atoms, halogen, or alkoxy of 1 to 4 carbon atoms;
$R^6$ is alkyl, alkenyl or alkynyl of 3 to 7 carbon atoms;
$R^7$ is heteroaryl selected from 2- and 3-thienyl, 2- and 3-furyl, 2-, 3-, and 4-pyridyl, p-biphenylyl; H, Cl, Br, I; $C_vF_{2v+1}$, where v=1-3;

straight or branched chain alkyl of 1 to 6 carbon atoms; or phenyl;
$R^8$ is

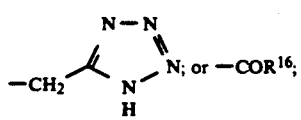

$R^{10}$ is CF$_3$, alkyl of 1 to 6 carbon atoms or pheny;
$R^{11}$ is H, or alkyl of 1 to 4 carbon atoms;
$R^{13}$ is CO$_2$H; CO$_2$CH$_2$OCOC(CH$_3$)$_3$; NHSO$_2$CF$_3$;

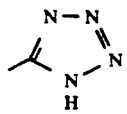

$R^{14}$ is H, or alkyl of 1 to 4 carbon atoms;
$R^{15}$ is H, alkyl of 1 to 4 carbon atoms, or acyl of 1 to 4 carbon atoms;
$R^{16}$ is H, alkyl of 1 to 5 carbon atoms; OR$^{17}$; or

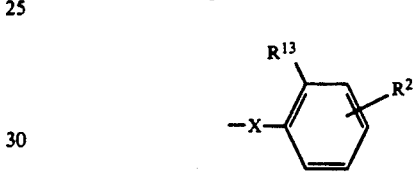

$R^{17}$ is H, alkyl of 1 to 6 carbon atoms or benzyl
m is 1 to 5;
X=single bond, —O—; —CO—; —NHCO—; or —OCH$_2$—; or a pharmaceutically acceptable salt thereof.

2. Method of claim 1 wherein the compound of formula II is a compound $R^1$ is

and X is a single bond; or a pharmaceutically suitable salt thereof.

3. Method of claim 2 wherein the compound of formula II is 2-Butyl-4-chloro-1-[(2'-(1H-tetrazol-5-yl)biphenyl-4-yl)methyl]-5-(hydroxymethyl)imidazole or a pharmaceutically acceptable salt thereof.

4. Method of claim 2 wherein the compound of formula II is 2-Butyl-4-chloro-1-[(2'-carboxybiphenyl-4-yl)-methyl]-5-(hydroxymethyl)imidazole or a pharmaceutically acceptable salt thereof.

5. Method of claim 2 wherein the compound of formula II is 2-Butyl-4-chloro-1-[(2'-carboxybiphenyl-4-yl)-methyl]-5-[(methoxycarbonyl)aminomethyl] imidazole or a pharmaceutically acceptable salt thereof.

6. Method of claim 2 wherein the compound of formula II is 2-Butyl-4-chloro-1-[(2'-carboxybiphenyl-4-yl) -methyl]-5-[(propoxycarbonyl)aminomethyl] imidazole or a pharmaceutically acceptable salt thereof.

7. Method of claim 2 wherein the compound of formula II is 2-Butyl-4-chloro-1-[(2'-carboxybiphenyl-4-yl) methyl]imidazole-5-carboxaldehyde or a pharmaceutically acceptable salt thereof.

8. Method of claim 2 wherein the compound of formula II is 2-Butyl-1-[(2'-carboxybiphenyl-4-yl)methyl]-imidazole-5-carboxaldehyde or a pharmaceutically acceptable salt thereof.

9. Method of claim 2 wherein the compound of formula II is 2-(1E-Butenyl)-4-chloro-1-[(2'-carboxybiphenyl -4-yl)methyl]-5-(hydroxymethyl)imidazole or a pharmaceutically acceptable salt thereof.

10. Method of claim 2 wherein the compound of formula II is 2-(1E-Butenyl)-4-chloro-1-[(2'-carboxybiphenyl -4-yl)methyl]imidazole-5-carboxaldehyde or a pharmaceutically acceptable salt thereof.

11. Method of claim 2 wherein the compound of formula II is 2-Propyl-4-chloro-1-[(2'-(1H-tetrazol-5- yl)biphenyl-4-yl)methyl]-5-(hydroxymethyl) imidazole or a pharmaceutically acceptable salt thereof.

12. Method of claim 2 wherein the compound of formula II is 2-Propyl-4-chloro-1-[(2'-(1H-tetrazol-5-yl)biphenyl-4-yl)methyl]imidazole-5-carboxaldehyde or a pharmaceutically acceptable salt thereof.

13. Method of claim 2 wherein the compound of formula II is 2-Butyl-4-chloro-1-[2'-(1H-tetrazol-5-yl)biphenyl-4-yl)methyl]imidazole-5-carboxaldehyde or a pharmaceutically acceptable salt thereof.

14. Method of claim 2 wherein the compound of formula II is 2-(1E-Butenyl)-4-chloro-1-[(2'-(1H-tetrazol-5-yl)biphenyl-4-yl)methyl]-5-hydroxymethyl-)imidazole or a pharmaceutically acceptable salt thereof.

15. Method of claim 2 wherein the compound of formula II is 2-(1E-Butenyl)-4-chloro-1-[(2'-(1H-tetrazol-5-yl)biphenyl-4-yl)methyl]imidazole-5-carboxaldehyde or a pharmaceutically acceptable salt thereof.

16. Method of claim 2 wherein the compound of formula II is 2-Butyl-4-chloro-1-[(2'-(1H-tetrazol-5-yl)-biphenyl-4-yl)methyl]imidazole-5-carboxylic acid or a pharmaceutically acceptable salt thereof.

17. Method of claim 2 wherein the compound of formula II is 2-Propyl-4-chloro-1-[(2'-(1H-tetrazol-5-yl)-biphenyl-4-yl)methyl]imidazole-5-carboxylic acid or a pharmaceutically acceptable salt thereof.

18. Method of claim 2 wherein the compound of formula II is 2-Propyl-4-trifluoromethyl-1-[(2'-(1H-tetrazol-5-yl)biphenyl-4-yl)methyl]imidazole-5-carboxylic acid or a pharmaceutically acceptable salt thereof.

19. Method of claim 2 wherein the compound of formula II is 2-Propyl-4-trifluoromethyl-1-[(2'-(1H-tetrazol-5-yl)biphenyl-4-yl)methyl]-5-(hydroxylmethyl)-imidazole or a pharmaceutically acceptable salt thereof.

20. Method of claim 2 wherein the compound of formula II is 2-Butyl-4-trifluoromethyl-1-[(2'-(1H-tetrazol-5-yl)biphenyl-4-yl)methyl]imidazole-5-carboyxlic acid or a pharmaceutically acceptable salt thereof.

21. Method of claim 2 wherein the compound of formula II is 2-Propyl-4-trifluoromethyl-1-[(2'-(carboxybiphenyl-4-yl)methyl]imidazole-5-carboxaldehyde or a pharmaceutically acceptable salt thereof.

22. Method of claim 2 wherein the compound of formula II is 2-Propyl-4-pentafluoroethyl-1-[(2'-(1H-tetrazol-5-yl)biphenyl-4-yl)methyl]-5-(hydroxymethyl)-imidazole or a pharmaceutically acceptable salt thereof.

23. Method of claim 2 wherien the compound of formula II is 2-Propyl-4-pentafluoroethyl-1-[(2'-(1H-tetrazol -5-yl)biphenyl-4-yl)methyl]imidazole-5-carboxylic acid or a pharmaceutically acceptable salt thereof.

24. Method of claim 2 wherein the compound of formula II is 2-Propyl-4-pentafluoroethyl-[(2'-(1H-tetrazol -5-yl)biphenyl-4-yl)methyl]imidazole-5-carboxaldehyde or a pharmaceutically acceptable salt thereof.

25. Method of claim 2 wherein the compound of formula II is 1-[(2'-(1H-Tetrazol-5-yl)biphenyl-4-yl)methyl]-4-phenyl -2-propylimidazole-5-carboxaldehyde.

26. Method of claim 2 wherein the compound of formula II is 1-[(2'-Carboxybiphenyl-4-yl)methyl]-4-phenyl-2-propylimidazole-5-carboxaldehyde.

* * * * *